US010352915B1

United States Patent
Kartalov et al.

(10) Patent No.: US 10,352,915 B1
(45) Date of Patent: Jul. 16, 2019

(54) SYSTEMS AND METHODS FOR EVALUATION OF POTENTIALLY IRRADIATED OBJECTS USING OXYGEN-17 DETECTION

(71) Applicant: The United States of America, as represented by the Secretary of the Navy, Washington, DC (US)

(72) Inventors: Emil Paskalev Kartalov, Pacific Grove, CA (US); Raymond M. Gamache, Prunedale, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 134 days.

(21) Appl. No.: 15/725,025

(22) Filed: Oct. 4, 2017

Related U.S. Application Data

(60) Provisional application No. 62/543,749, filed on Aug. 10, 2017.

(51) Int. Cl.
*G01N 33/00* (2006.01)
*G01N 24/08* (2006.01)
(Continued)

(52) U.S. Cl.
CPC ......... *G01N 33/0036* (2013.01); *G01N 24/08* (2013.01); *G01N 30/7206* (2013.01); *G01N 2030/025* (2013.01); *H01J 49/0027* (2013.01)

(58) Field of Classification Search
CPC ................................................. G01N 33/0036
See application file for complete search history.

(56) References Cited

U.S. PATENT DOCUMENTS

| 5,184,019 A | 2/1993 | MacArthur et al. |
| 5,187,370 A | 2/1993 | MacArthur et al. |

(Continued)

OTHER PUBLICATIONS

Wassenaar et al., "An On-Line Technique for the Determination of the $\delta 18O$ and $\delta 17O$ of Gaseous and Dissolved Oxygen," Anal. Chem. 71 (1999).

(Continued)

*Primary Examiner* — Lisa M Caputo
*Assistant Examiner* — Alex T Devito
(74) *Attorney, Agent, or Firm* — Naval Postgraduate School; Scott Bell

(57) ABSTRACT

A system for detection of a potentially irradiated object utilizing oxygen-17 ($^{17}O$) quantities in a local atmosphere contacting the potentially irradiated object. The local atmosphere comprises nitrogen-14 ($^{14}N$) and is typically air. The $^{17}O$ quantity in the local atmosphere is determined through sampling using mass spectroscopy, nuclear resonance magnetic imaging, gas chromatography, or some other method. The $^{17}O$ quantity in the local atmosphere is compared to a baseline quantity of $^{17}O$ and deviations are treated as an indicator that a nuclear reaction converting $^{14}N$ to $^{17}O$ has occurred or is occurring. Typically the local atmosphere is isolated to some degree from an external atmosphere via some type of enclosure or container, and the external atmosphere provides the baseline quantity of $^{17}O$ used for the comparison.

20 Claims, 4 Drawing Sheets

(51) Int. Cl.
  *H01J 49/00* (2006.01)
  *G01N 30/72* (2006.01)
  *G01N 30/02* (2006.01)

(56) References Cited

U.S. PATENT DOCUMENTS

| | | |
|---|---|---|
| 5,194,737 A | 3/1993 | MacArthur et al. |
| 5,311,025 A | 5/1994 | MacArthur et al. |
| 5,433,196 A * | 7/1995 | Fiat .................... G01R 33/5601 600/410 |
| 5,705,818 A | 1/1998 | Kelbel et al. |
| 6,891,470 B2 | 5/2005 | Bohinc, Jr. |
| 7,151,447 B1 | 12/2006 | Willms et al. |

OTHER PUBLICATIONS

Yueng et al., "Measurements of 18O18O and 17O18O in the atmosphere and the role of isotope-exchange reactions," J. Geophys. Res., 117 (2012).

Abe et al., "Partial pressure dependency of 17O/16O and 18O/16O of molecular oxygen in the mass spectrometer," Rapid Commun. Mass Spectrom. 17 (2003).

Mrozek et al., "Continuous-flow IRMS technique for determining the 17O excess of CO2 using complete oxygen isotope exchange with cerium oxide," Atmos. Meas. Tech. 8 (2015).

Muccio et al., "Isotope ratio mass spectrometry," Analyst 134 (2009).

Werner et al., "Referencing strategies and techniques in stable isotope ratio analysis," Rapid Commun. Mass Spectrom. 15 (2001).

Young et al., "Isotope-ratio-monitoring of O2 for microanalysis of 18O/16O and 17O/16O in geological materials," Geochimica et Cosmochimica Acta, 62(18) (1998).

Baker et al., "A Technique for the Determination of 18O/16O and 17O/16O Isotopic Ratios in Water from Small Liquid and Solid Samples," Anal. Chem. 74 (2002).

MacArthur et al., "Long-Range Alpha Detector (LRAD) Technology, Results, and Applications," Nuclear Science Symposium and Medical Imaging Conference, 1992., Conference Record of the 1992 IEEE (1992).

MacArthur et al., "Small Long Range Alpha Detector (LRAD) with Computer Readout," LA-12199-MS, available at https://www.osti.gov/scitech/servlets/purl/5090469 last accessed Sep. 15, 2017.

* cited by examiner

SYSTEMS AND METHODS FOR EVALUATION OF POTENTIALLY IRRADIATED OBJECTS USING OXYGEN-17 DETECTION

RELATION TO OTHER APPLICATIONS

This patent application is a nonprovisional of and claims benefit from U.S. Provisional application 62/543,749 filed Aug. 10, 2017, which is hereby incorporated by reference in its entirety.

FIELD OF THE INVENTION

One or more embodiments relates generally to the evaluation of potentially irradiated objects through detection of $^{17}O$ in an atmosphere surrounding a potentially irradiated object.

BACKGROUND

Alpha particles are emitted by a wide range of heavy nuclei, which are responsible for a large proportion of radioactive materials required to be monitored. Furthermore, alpha particles are potentially the most damaging type of radiation to biological tissue due to their high mass and relatively high energy. However, alpha particles are difficult to detect since they are readily absorbed in materials and biological tissue, and even in air can travel no more than a few centimeters from the radioactive source material. Thus, typical detectors for alpha particles have to be brought very close to the scanned items, which makes scanning slow, cumbersome, or even impractical in many common environments.

As a result, the ability to scan fast, reliably, and specifically for alpha particles especially in relatively confined complex-geometry terrain, e.g. ground vehicles, maritime vessels, shipping containers, and aircraft, would be a valuable asset. Furthermore, in a forensic sense, it would be useful to provide a system capable of determining if a nuclear material was present at some certain point in the past.

The system disclosed here provides for the detection of nuclear materials and/or potentially irradiated objects through evaluation of oxygen-17 ($^{17}O$) quantities in a local atmosphere. The local atmosphere sampled is in contact with the material or object under evaluation and typically comprises air. The $^{17}O$ quantity in the local atmosphere is determined using mass spectroscopy, nuclear resonance magnetic imaging, gas chromatography, or some other method, and deviations in $^{17}O$ quantity relative to an expected baseline are treated as indicative that a nuclear reaction converting nitrogen-14 ($^{14}N$) to $^{17}O$ has occurred or is occurring.

These and other objects, aspects, and advantages of the present disclosure will become better understood with reference to the accompanying description and claims.

SUMMARY

The disclosed system and method provides for detection of potentially irradiated objects through evaluation of $^{17}O$ quantities in a local atmosphere in fluid communication with the object. Object in this sense refers generally to a discrete object, the interior of a container, a collection of items grouped in a local proximity, a radioactive source in and of itself, or any other discrete physical matter in contact with the sampled atmosphere. The local atmosphere contacting the object comprises $^{14}N$ and typically comprises air, and the $^{17}O$ quantity in the local atmosphere is determined through sampling using mass spectroscopy, nuclear resonance magnetic imaging, gas chromatography, or some other method. The $^{17}O$ quantity in the local atmosphere is compared to a baseline quantity of $^{17}O$ and deviations are treated as an indicator that a nuclear reaction converting $^{14}N$ to $^{17}O$ has occurred or is occurring. Typically the local atmosphere is isolated to some degree from an external atmosphere via some type of enclosure or container, and the external atmosphere provides the baseline quantity of $^{17}O$ used for the comparison.

Implementation of the method generally comprises sampling a surrounding atmosphere comprising $^{14}N$ and in contact with an object and thereby generating an atmospheric sample, providing the atmospheric sample to an atmospheric analyzer, determining a quantity of $^{17}O$ in the atmospheric sample using the atmospheric analyzer, comparing the quantity of $^{17}O$ in the atmospheric sample to a baseline quantity of $^{17}O$, and, if the quantity of $^{17}O$ in the atmospheric sample is greater than or equal to the baseline quantity of $^{17}O$, designating the object as a potentially irradiated object.

A system for implementation of the method generally comprises a sampling line withdrawing an atmospheric sample from a surrounding atmosphere comprising $^{14}N$, further comprises an atmospheric analyzer configured to receive and provide a quantity of $^{17}O$ in the atmospheric sample, and further comprises a digital processor in data communication with the atmospheric analyzer. The digital processor is programmed to perform steps comprising: (i) receiving the quantity of $^{17}O$ in the atmospheric sample from atmospheric analyzer 104; (ii) comparing the quantity of $^{17}O$ in the atmospheric sample to a baseline quantity of $^{17}O$; and (iii) generating an alert signal if the quantity of $^{17}O$ in the atmospheric sample is greater than or equal to the baseline quantity of $^{17}O$. The system further comprises an alarming device in data communication with digital processor configured to receive the alert signal and provide an alarm in response to the alert signal.

The novel apparatus and principles of operation are further discussed in the following description.

Figure 1:
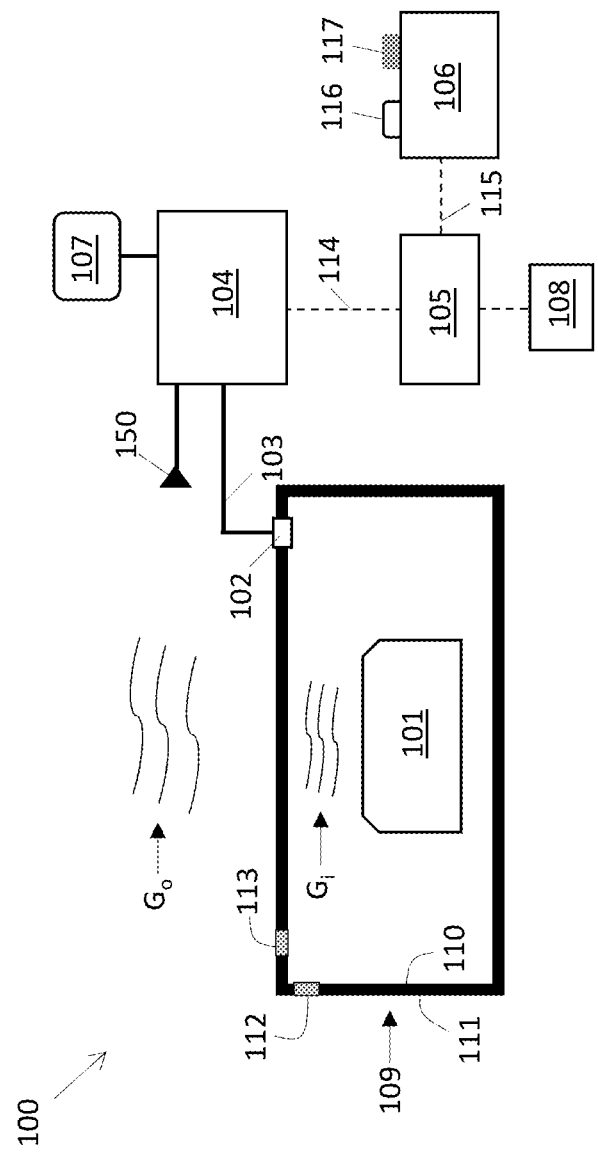
FIG. 1 illustrates an embodiment of the detection system.

Embodiments in accordance with the invention are further described herein with reference to the drawings.

DETAILED DESCRIPTION OF THE INVENTION

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a system and method for the detection of potentially irradiated objects through monitoring of $^{17}$O concentration in a local environment.

The disclosed system and method provides for detection of potentially irradiated object through evaluation of $^{17}$O quantities in a local atmosphere contacting the object. Briefly, the local atmosphere contacting the object comprises $^{14}$N and typically comprises air, and the $^{17}$O quantity in the local atmosphere is determined through sampling using mass spectroscopy, nuclear resonance magnetic imaging, gas chromatography, or some other method. The $^{17}$O quantity in the local atmosphere is compared to a baseline quantity of $^{17}$O and deviations are treated as an indicator that a nuclear reaction converting $^{14}$N to $^{17}$O has occurred or is occurring. Typically the local atmosphere is isolated to some degree from an external atmosphere via some type of enclosure or container, and the external atmosphere provides the baseline quantity of $^{17}$O used for the comparison.

As is understood, alpha particles a released from radiative emitters interact with surrounding gases comprising $^{14}$N by a well-known reaction:

$$^{14}N + \alpha \rightarrow {}^{17}O + p$$

The system disclosed exploits atmospheres comprising $^{14}$N and in contact with an object in order to detect $^{17}$O concentrations above an expected value. $^{17}$O concentrations above expected values are treated as indicative that the above nuclear reaction may have occurred in a sampled atmosphere due to contact between the sampled atmosphere and a radioactive source. Correspondingly, for $^{17}$O concentrations higher than expected, the detection system disclosed similarly infers that other objects also in contact with the sampled atmosphere may be or may have been subject to alpha radiation, and designates such objects as potentially irradiated objects. As is discussed further below, "object" in this sense may mean a discrete object, the interior of a container, a collection of items grouped in a local proximity, a radioactive source in and of itself, or any other discrete physical matter in contact with the sampled atmosphere.

Because atmospheric air is generally about 80% nitrogen with 99.6% of that nitrogen as $^{14}$N, in typical embodiments the system disclosed utilizes air. Air generally ensures as cheap and easy operation as possible, since the working gas is then readily available from the atmosphere, completely eliminating gas-related costs and supply chain. Additionally, using atmospheric air as the working gas may eliminate the need for a pumper or blower as a vacuum collector alone may be enough to produce the necessary gas flow. Using just the collector would simplify the system and allow easier and more convenient access to the sampled space.

$^{17}$O is an excellent candidate as a reporter of the nuclear reaction for several reasons. First, $^{17}$O is extremely rare in the natural environment, with an abundance less than 0.04% in sea water. Thus, any significant increase is measurable reliably and with high sensitivity. Second, $^{17}$O is stable. This means that the air already trapped in a container or vehicle will have an accumulation of $^{17}$O as alpha particles are emitted and interact with the $^{14}$N present, generating native air heavily enriched with $^{17}$O and making detection by the disclosed system more reliable. Further, due to the accumulation, even if a source is subsequently removed, there would be a leftover signature to indicate a past presence. Third, $^{17}$O is the only stable isotope of oxygen that also has a non-zero spin (+5/2). Thus, $^{17}$O can be identified through analysis methods such as nuclear magnetic resonance (NMR).

A typical embodiment of the system disclosed is illustrated at FIG. 1. At FIG. 1 illustrates a detection system generally indicated at 100 and depicts an object 101 in contact with a surrounding atmosphere $G_i$. The surrounding atmosphere $G_i$ comprises a gas comprising nitrogen-14 ($^{14}$N), such as air. A sampling line 103 is in fluid communication with surrounding atmosphere $G_i$ via nozzle 102, and in the depicted embodiment additionally in fluid communication with atmospheric analyzer 104. Atmospheric analyzer 104 comprises a device capable of analyzing a gaseous sample for the presence of oxygen-17 ($^{17}$O), such as a mass spectrometer, a nuclear magnetic resonance spectrometer (NMR), or a gas chromatograph. In some embodiments, detection system 100 further comprises a second sample line 106 in fluid communication with atmospheric analyzer 104 and additionally in fluid communication with an external atmosphere $G_o$ comprising $^{14}$N, such as air. In typical embodiments, an enclosure generally indicated at 109 comprises an interior surface 110 at least partially surrounding the surrounding atmosphere $G_i$ such that surrounding atmosphere $G_i$ resides within an interior of enclosure 109, and further comprises an exterior 111 surface in contact with the external atmosphere $G_o$, such that surrounding atmosphere $G_o$ contacts an exterior of enclosure 109. In other embodiments, atmospheric analyzer 104 is in fluid communication with a sample of external atmosphere $G_o$ where the sample is surrounded by vessel 107.

Implementation of the method disclosed generally comprises inspecting an object such as object 101 by sampling surrounding atmosphere $G_i$ in fluid communication with object 101 in order to generate an atmospheric sample. For example, generating the atmospheric sample by sampling surrounding atmosphere $G_i$ through nozzle 102 and sampling line 103. The method further comprises generally providing the atmospheric sample to atmospheric analyzer 104, for example via sampling line 103, and analyzing the atmospheric sample using atmospheric analyzer 104. The method further comprises comparing the quantity of $^{17}$O in the atmospheric sample determined by atmospheric analyzer 104 to a baseline quantity of $^{17}$O. The method further comprises designating object 101 as a potentially irradiated object depending on the comparison of the $^{17}$O quantity of the atmospheric sample derived from surrounding atmosphere $G_i$ with the baseline quantity of $^{17}$O. Typically the baseline quantity of $^{17}$O reflects an $^{17}$O quantity in the external atmosphere $G_o$. In general embodiments, if the quantity of $^{17}$O in the atmospheric sample is greater than the baseline quantity of $^{17}$O, the object is designated as a potentially irradiated object. In contrast, if the quantity of $^{17}$O in the atmospheric sample is equal to or less than the baseline quantity of $^{17}$O, the object is designated as a non-potentially irradiated object. Thus, detection system 100 provides a method for detecting a potentially irradiated object such as object 101 using $^{17}$O detection.

As used here, "irradiated object" means an object which has been exposed to ionizing radiation in the past, or which is itself presently emitting an ionizing radiation, or which is presently in proximity to a source emitting an ionizing radiation. As such, an irradiated object within this disclosure might refer to an object which has been exposed to, for example, alpha radiation from an alpha source subsequently removed, or may refer to the alpha source itself currently emitting the alpha radiation, or may refer to an object in current proximity to the alpha source. Correspondingly, in certain embodiments, detection system 100 provides a method of detecting a present or past source of alpha radiation which co-exists or co-existed in relatively close proximity to an object such as object 101. Here the term "object" is not intended to be strictly limiting and may mean

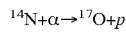

an object which is separate and distinct from a surrounding enclosure such as enclosure 109, or alternately may refer to some portion of enclosure 109, such as some portion of interior surface 110, or may refer to a radioactive source in and of itself or any other discrete physical matter in contact with the sampled atmosphere, or any combination of the preceding. Additionally, although represented as an isolated object within enclosure 109 at FIG. 1, object 101 may be present with neighboring objects such that a collection of various objects may be evaluated as a group by detection system 100.

As discussed and in certain embodiments comprising an enclosure such as enclosure 109, enclosure 109 comprises interior surface 110 with interior surface 110 at least partially surrounding atmosphere $G_i$, such that surrounding atmosphere $G_i$ resides within the interior of enclosure 109. The interior of enclosure 109 may provide a complete closure around surrounding atmosphere $G_i$ such that surrounding atmosphere $G_i$ is isolated from external atmosphere $G_o$, or the interior of enclosure 109 may form a cavity having an opening which allows limited fluid communication between surrounding atmosphere $G_i$ and external atmosphere $G_o$. In an embodiment, when enclosure 109 includes one or more flow areas establishing fluid communication between surrounding atmosphere $G_i$ and external atmosphere $G_o$, the combined total area of all flow areas present is less than 50%, in some embodiments less than 25%, and in other embodiments less than 10% of the combined total area of the interior of the enclosure. For example at FIG. 1, enclosure 109 comprises flow areas 112 and 113 providing some degree of fluid communication between surrounding atmosphere $G_i$ and external atmosphere $G_o$. and the combined total area of flow areas 112 and 113 is less than 50%, less than 25%, and/or less than 10% of the combined total area of the interior 110 of enclosure 109. As is understood, such situations can arise when the enclosure is, for example, a vented cargo container, an automobile with a door partially or fully open, or other situations which might be envisioned. It is additionally understood that within the system and method disclosed, the term "enclosure" is not limited to artificial, fabricated containers specifically constructed and intended to hold certain items, but extends to any structure natural or otherwise. For example, detection system 100 might be utilized by taking atmospheric samples over a pitted or cracked planar surface where the pitting or cracks function as an enclosure providing increased $^{17}O$ concentration due to contamination by radioactive material, or might be utilized by inserting nozzle 102 deep within a randomly assorted collection of items such that the surrounding assortment of items functions as an enclosure.

In certain embodiments where an external atmosphere $G_o$ is in contact with the exterior 111 of enclosure 109, the baseline quantity of $^{17}O$ which provides comparison for the quantity of $^{17}O$ in enclosure 109 is based on the quantity of $^{17}O$ in external atmosphere $G_o$. Correspondingly, in specific embodiments, the method disclosed further comprises sampling the external atmosphere $G_o$ to generate an external atmosphere sample, analyzing the external atmosphere sample with atmospheric analyzer 104 to determine a quantity of $^{17}O$ in the external sample, and designating the quantity of $^{17}O$ in the external sample as the baseline quantity of $^{17}O$ against which the atmospheric sample derived from surrounding atmosphere $G_i$ is compared. Here it is understood that, when based on sampling the external atmosphere $G_o$, the baseline quantity of $^{17}O$ determined may be based on a single $G_o$ sample or may be a combination of multiple $G_o$ samples, and that the term "external atmosphere sample" may correspondingly refer to a single sample or a plurality of samples. Additionally, when the baseline quantity of $^{17}O$ is based on a plurality of $G_o$ samples, the individual samples may be taken over a variety of times and general locations in order to determine the baseline quantity of $^{17}O$. In certain embodiments, detection system 100 comprises second sample line 150 in fluid communication with external atmosphere $G_o$ and external atmosphere samples are taken and delivered to atmospheric analyzer 104 through second sample line 150. In other embodiments, external atmosphere samples are taken and analyzed by establishing fluid communication between sample line 103 and external atmosphere $G_o$ either before or after establishing fluid communication with surrounding atmosphere $G_i$ to draw the atmospheric sample.

Atmospheric analyzer 104 may be any device capable of receiving samples comprising some portion of an atmosphere, determining a quantity of $^{17}O$ in the received sample, and providing an output corresponding to the quantity of $^{17}O$ in the received sample. For example, in certain embodiments, atmospheric analyzer 104 comprises at least one of a mass spectrometer, a nuclear magnetic resonance spectrometer, a gas chromatograph, or some combination therein. It is additionally understood that atmospheric analyzer 104 may comprise additional devices necessary to prepare an atmospheric sample for $^{17}O$ analysis, such as cryogenic separators, dehumidifiers, and other conditioning equipment. Methods of operating the applicable devices for the detection of $^{17}O$ or derivation of a $^{17}O$ value based on $^{18}O$ determination in a sample are known in the art. See e.g., Wassenaar et al., "An On-Line Technique for the Determination of the $\delta^{18}O$ and $\delta^{17}O$ of Gaseous and Dissolved Oxygen," *Anal. Chem.* 71 (1999); see also Yueng et al., "Measurements of $^{18}O^{18}O$ and $^{17}O^{18}O$ in the atmosphere and the role of isotope-exchange reactions," *J. Geophys. Res.*, 117 (2012); see also Abe et al., "Partial pressure dependency of $^{17}O/^{16}O$ and $^{18}O/^{16}O$ of molecular oxygen in the mass spectrometer," *Rapid Commun. Mass Spectrom.* 17 (2003); see also Mrozek et al., "Continuous-flow IRMS technique for determining the $^{17}O$ excess of $CO_2$ using complete oxygen isotope exchange with cerium oxide," *Atmos. Meas. Tech.* 8 (2015); see also Muccio et al., "Isotope ratio mass spectrometry," *Analyst* 134 (2009); see also Werner et al., "Referencing strategies and techniques in stable isotope ratio analysis," *Rapid Commun. Mass Spectrom.* 15 (2001); see also P. A. de Groot, *Handbook of Stable Isotope Analytical Techniques*, (2008), among others.

The specific embodiment of the system illustrated at FIG. 1 comprises atmospheric analyzer 104 configured to receive the atmospheric sample from sampling line 103, determine a quantity of $^{17}O$ in the atmospheric sample, and provide an output corresponding to the quantity of $^{17}O$ in the atmospheric sample. The system further comprises a digital processor 105 in data communication with atmospheric analyzer 104 via 114, where digital processor 105 is programmed to at least perform steps comprising: (i) receiving the quantity of $^{17}O$ in the atmospheric sample from atmospheric analyzer 104; (ii) comparing the quantity of $^{17}O$ in the atmospheric sample to a baseline quantity of $^{17}O$; and (iii) generating an alert signal if the quantity of $^{17}O$ in the atmospheric sample is greater than the baseline quantity of $^{17}O$. The system further comprises alarming device 106 in data communication with digital processor 105 via 115. Alarming device 106 is configured to receive the alert signal and provide an alarm in response to the alert signal, where typically the alarm is visual, audible, or some combination therein. For example at FIG. 1, alarming device 106 provides a visual alarm 116, an audible alarm via 117, or some combination. Alarming device 106 may be configured to provide an alarm in response to a digital signal, analog signal, or some combination provided by digital processor 105. The system thereby provides a relatively automated system whereby an object can be monitored and an observer visually alerted if object 101 is a potentially irradiated object.

In certain embodiments of the system, digital processor 105 is further programmed to receive the baseline quantity of $^{17}O$ used in the comparison from atmospheric analyzer 104. In further embodiments, the system comprises sampling line 103 withdrawing an atmospheric sample from surrounding atmosphere $G_i$ in the interior of enclosure 109 and additionally comprises second sampling line 150 in fluid communication with external atmosphere $G_o$, with second sampling line 150 configured to withdraw and deliver an external atmospheric sample to atmospheric analyzer 104. In this embodiment, atmospheric analyzer 104 receives the external atmospheric sample and determines a quantity of $^{17}O$ in the external atmospheric sample. Digital processor 105 is further programmed to receive the quantity of $^{17}O$ in the external atmospheric sample and designate the quantity of oxygen-17 in the external atmospheric sample as the baseline quantity of oxygen-17 against which atmospheric samples derived from surrounding atmosphere $G_i$ will be compared. In a further embodiment, digital processor 105 is programmed to receive the baseline quantity of $^{17}O$ from input device 108.

Figure 2:
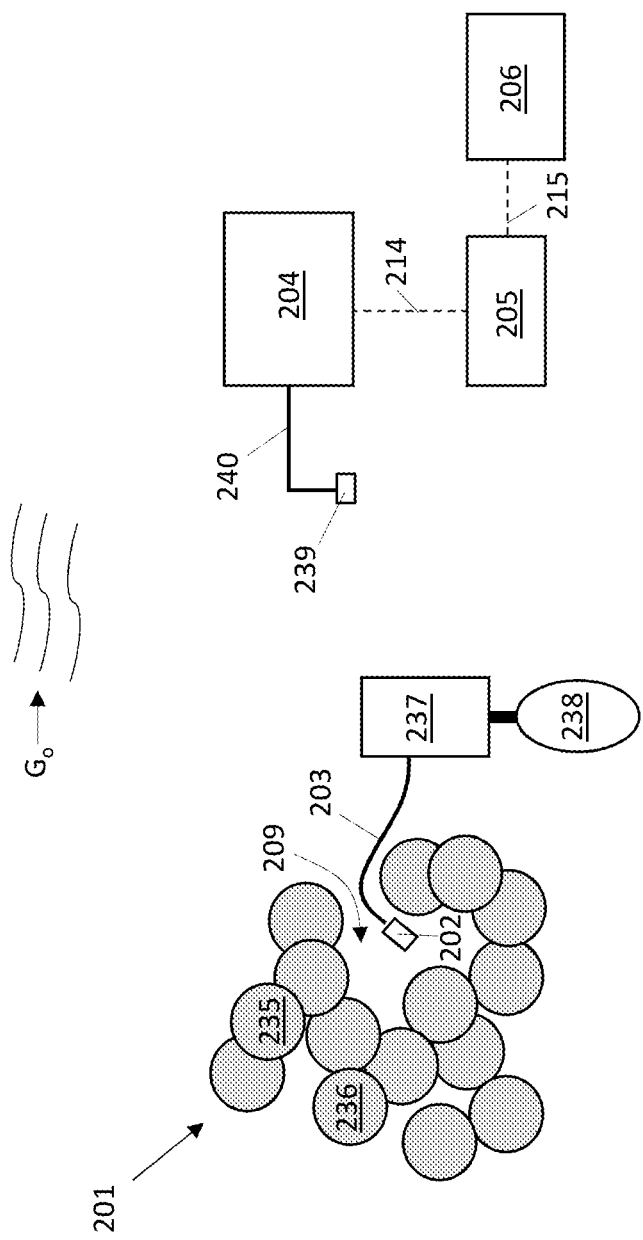
FIG. 2 illustrates another embodiment of the detection system.

Another embodiment of the system is illustrated at FIG. 2. The detection system depicted comprises nozzle 202 in fluid communication with sample line 203, and sample line 203 in fluid communication with sniffer unit 237 configured to deliver samples to reservoir 238. The detection system further comprises fitting 239 and sample intake 240 in fluid communication with atmospheric analyzer 204, and digital processor 205 in data communication with atmospheric analyzer 204 via 214 and alarming device 206 via 215. At FIG. 2, the detection system evaluates a collection of objects generally indicated by 201 and comprising individual objects such as 235 and 236. The collection of objects 201 is in a complex terrain providing relatively isolated enclosures such as that indicated generally by 209. In this particular embodiment, nozzle 202 samples a surrounding atmosphere $G_i$ (not shown) within the interior of enclosure 209 to provide an atmospheric sample to reservoir 238 via sample line 203 and sniffer unit 237. Reservoir 238 is subsequently placed in fluid communication with fitting 239 and sample intake 240 to enable $^{17}O$ analysis by atmospheric analyzer 204. As before, atmospheric analyzer 204 provides a quantity of $^{17}O$ in the atmospheric sample and provides the quantity of $^{17}O$ in the atmospheric sample to digital processor 205, which evaluates the quantity of $^{17}O$ in the atmospheric sample against a baseline quantity of $^{17}O$ and generates an alert to alarming device 206 based on the comparison. In certain embodiments, the baseline quantity of $^{17}O$ reflects a quantity of $^{17}O$ within external atmosphere $G_o$. Additionally as illustrated, the complex terrain afforded by the collection of objects 201 allows limited fluid communication between external atmosphere $G_o$ and surrounding atmosphere $G_i$ however generally the combined flow areas establishing the limited fluid communication is less than 50%, less than 25%, and/or less than 10% of the combined total area of the interior of enclosure 209 formed by the various objects. Additionally, it is understood that although the atmospheric sample may be delivered to atmospheric analyzer 204 directly as described, intervening transfers of the atmospheric sample may also occur before the atmospheric sample is ultimately delivered to fitting 239.

Figure 3:
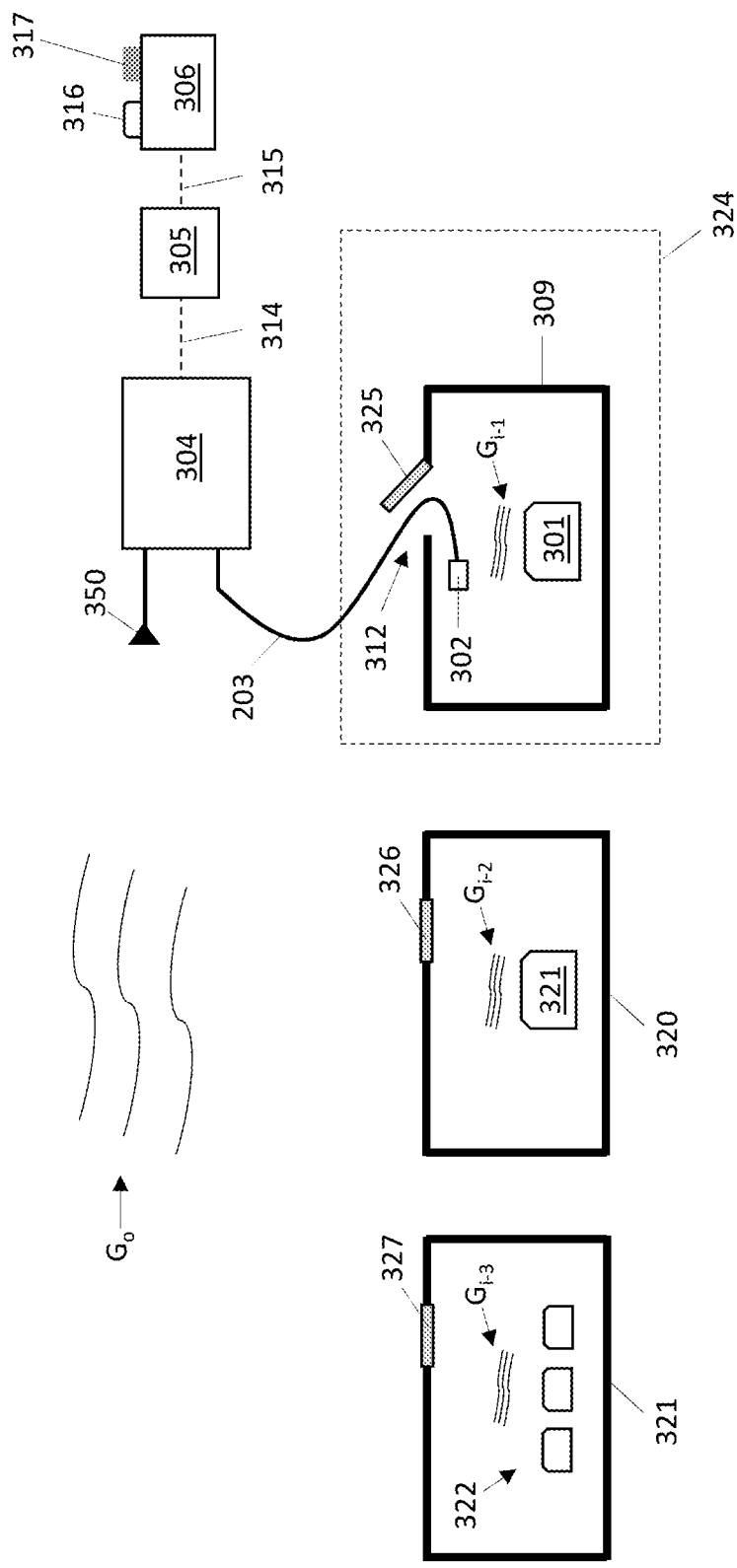
FIG. 3 illustrates an additional embodiment of the detection system.

The method and system additionally lends itself to efficiently and individually evaluating a plurality of objects in order to detect past or present exposure to irradiation. For example, FIG. 3 illustrates containers 309, 310, and 311 holding objects indicated by 301, 321, and generally by 322. Each container 309, 310, and 311 has an individual surrounding atmospheres annotated as $G_{i-1}$, $G_{i-2}$, and $G_{i-3}$ respectively, and each has some form of access hatch to the respective interiors, illustrated at FIG. 3 as 325, 326, and 327. An external atmosphere $G_o$ is additionally illustrated and in contact with the exterior of each of 309, 310, and 311. Each of the surrounding atmospheres $G_{i-1}$, $G_{i-2}$, and $G_{i-3}$ and external atmosphere $G_o$ comprise air, and thereby comprise $^{14}N$. The system as illustrated comprises nozzle 302 and sampling line 303 in fluid communication with atmospheric analyzer 304, digital processor 305 in data communication with atmospheric analyzer 304 via 314, and alarm device 306 in data communication with digital processor 305 via 315. In order to evaluate the plurality of objects 301, 321, and 322, each individual surrounding atmosphere $G_{i-1}$, $G_{i-2}$, and $G_{i-3}$ is sampled individually and separately. For example, at FIG. 3 and in order to evaluate object 301, sample line 303 and nozzle 302 are placed in fluid communication with individual surrounding atmosphere $G_{i-1}$ by opening access hatch 325, and an atmospheric sample indicative of $G_{i-1}$ is provided to atmospheric analyzer 304. Atmospheric analyzer 304 analyzes and determines a quantity of $^{17}O$ in the atmospheric sample and provides the quantity of $^{17}O$ in the atmospheric sample to digital processor 305. Digital processor 305 compares the quantity of $^{17}O$ in the atmospheric sample to a baseline quantity of $^{17}O$, and designates object 301 as a potentially irradiated object or non-potentially irradiated object based on the comparison of the $^{17}O$ quantity of the atmospheric sample and a baseline quantity of $^{17}O$, typically derived from external atmosphere $G_o$. Depending on the comparison, digital processor provides an alert signal to alarming device 306 to initiate visual alarm 316, audio alarm 317, or some other type of alarm to an operator.

Following evaluation of object 310, object 321 of container 320 is inspected in a similar manner by sampling surrounding atmosphere $G_{i-2}$ via its access hatch 326, and object 322 of container 321 is inspected in a similar manner by sampling surrounding atmosphere $G_{i-3}$ via its access hatch 327. As before, opening the access hatches 325, 326, and 327 in turn provides some degree of fluid communication between the respective surrounding atmospheres $G_{i-1}$, $G_{i-2}$, and $G_{i-3}$ and external atmosphere $G_o$, however the flow areas established through each hatch is less than 50%, less than 25%, and/or less than 10% of the combined total area of the interior of the applicable containers.

Additionally it is understood that alternatively, individual evaluation of objects 301, 321, and 322 could be performed in the absence of containers 309, 321, and 322 by placing each specific object individually in an enclosure such as inspection station enclosure 324, allowing a surrounding atmosphere in contact with the specific object to generate in inspection station enclosure 324, sampling the surrounding atmosphere to generate an atmospheric sample for the specific object, and comparing the quantity of $^{17}O$ in the atmospheric sample to a baseline quantity of $^{17}O$, as before. For example, objects 301, 321, and 322 could be a group of controlled items required to undergo various evaluations during the course of screening for Naturally Occurring Radioactive Materials (NORM) or Technologically Enhanced Naturally Occurring Radioactive Materials (TENORM).

Figure 4:
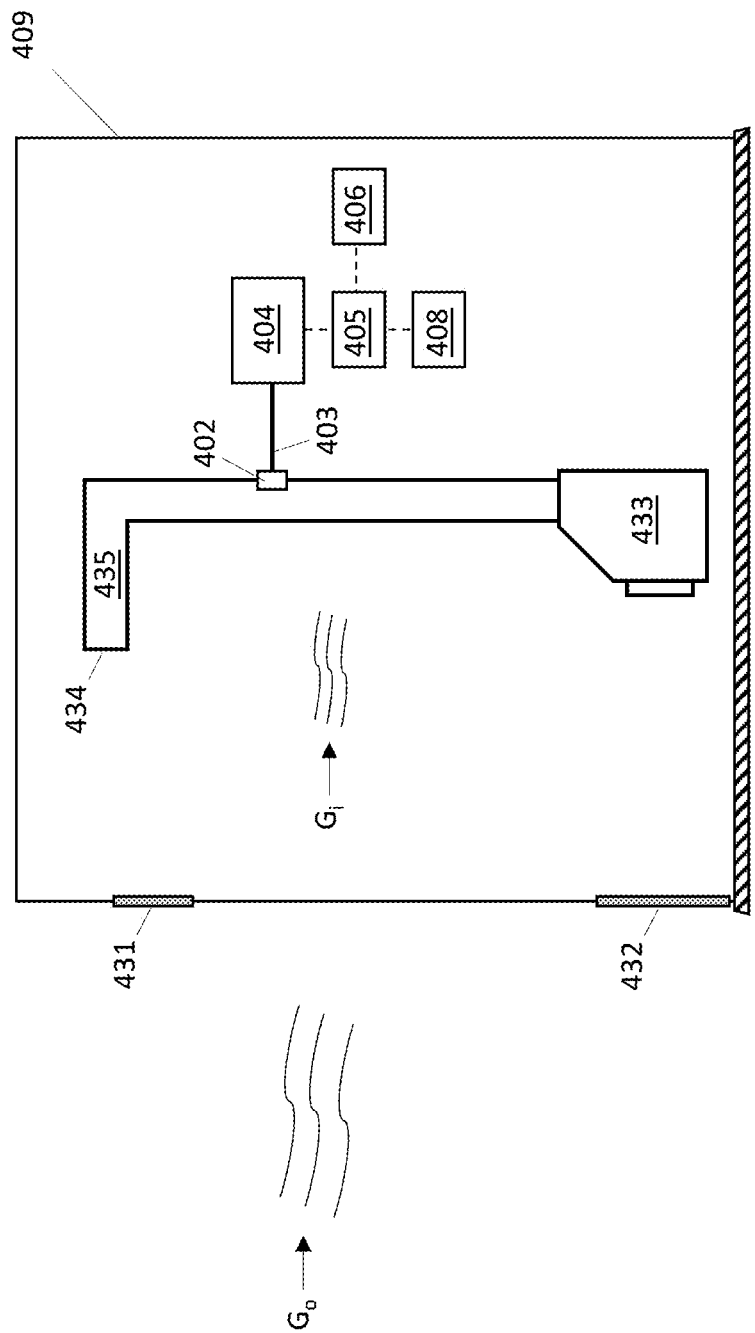
FIG. 4 illustrates a further embodiment of the detection system.

A further embodiment of the detection system is illustrated at FIG. 4, representing a building or other enclosed space having some degree of isolation from an external atmosphere. At FIG. 4, building 409 establishes a surrounding atmosphere $G_i$ with intermittent or limited fluid communication with an external atmosphere $G_o$ through, for example, window 431 or entrance 432. A ventilation system 433 circulates surrounding atmosphere $G_i$ within building 409 using intake 434 and ducting 435. A detection system comprises nozzle 402 establishes fluid communication between ducting 435 and sampling line 403, with sampling line 403 in fluid communication with atmospheric analyzer 404. Atmospheric analyzer 404 is in data communication with digital processor 405, and digital processor 405 is in data communication with input device 408 and alarm device 406. In operation, the system periodically samples surrounding atmosphere $G_i$ via nozzle 402 and sampling line 403. Atmospheric analyzer 404 determines a quantity of $^{17}O$ in surrounding atmosphere $G_i$ and provides results to digital processor 405. Digital processor 405 compares the quantity of $^{17}O$ in surrounding atmosphere $G_i$ against a baseline provided by input device 408, and generates alerts to alarm system 406 based on the comparison, as before. In typical practice, the baseline provided by input device 408 is based on a quantity of $^{17}O$ in external atmosphere $G_o$, and the combined flow areas establishing limited fluid communication between external atmosphere $G_o$ and surrounding atmosphere $G_i$ via window 431 and entrance 432 is less than 50%, less than 25%, and/or less than 10% of the combined total area of the interior of building 409.

Thus provided here is a system and method for detection of potentially irradiated object through evaluation of oxygen-17 ($^{17}O$) quantities in a local atmosphere. The local atmosphere contacting the potentially irradiated object comprises nitrogen-14 ($^{14}N$) and typically comprises air, and the $^{17}O$ quantity in the local atmosphere is determined through sampling using mass spectroscopy, nuclear resonance magnetic imaging, gas chromatography, or some other method. The $^{17}O$ quantity in the local atmosphere is compared to a baseline quantity of $^{17}O$ and deviations are treated as an indicator that a nuclear reaction converting $^{14}N$ to $^{17}O$ has occurred or is occurring. Typically the local atmosphere is isolated to some degree from an external atmosphere via some type of enclosure or container, and the external atmosphere provides the baseline quantity of $^{17}O$ used for the comparison.

Accordingly, this description provides exemplary embodiments of the present invention. The scope of the present invention is not limited by these exemplary embodiments. Numerous variations, whether explicitly provided for by the specification or implied by the specification or not, may be implemented by one of skill in the art in view of this disclosure.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of inspecting an object for possible irradiation exposure comprising:
    sampling a surrounding atmosphere, where the surrounding atmosphere contacts the object and where the surrounding atmosphere comprises nitrogen-14, thereby collecting an atmospheric sample;
    analyzing the atmospheric sample with an atmospheric analyzer and determining a quantity of oxygen-17 in the atmospheric sample;
    comparing the quantity of oxygen-17 in the atmospheric sample to a baseline quantity of oxygen-17;
    designating, if the quantity of oxygen-17 in the atmospheric sample is greater than the baseline quantity of oxygen-17, the object as a potentially irradiated object, or designating, if the quantity of oxygen-17 in the atmospheric sample is equal to or less than the baseline quantity of oxygen-17, the object as a non-potentially irradiated object, thereby inspecting the object for possible irradiation exposure.

2. The method of claim 1 where the object and the surrounding atmosphere reside in an interior of an enclosure and further comprising sampling the surrounding atmosphere by sampling the interior of the enclosure.

3. The method of claim 2 where an external atmosphere is in contact with an exterior of the enclosure and where the external atmosphere comprises nitrogen-14, and further comprising establishing the baseline quantity of oxygen-17 based on a quantity of oxygen-17 comprising the external atmosphere of the enclosure.

4. The method of claim 3 further comprising:
    sampling the external atmosphere thereby generating an external atmospheric sample;
    analyzing the external atmospheric sample with the atmospheric analyzer and determining a quantity of oxygen-17 in the external atmospheric sample; and
    designating the quantity of oxygen-17 in the external atmospheric sample as the baseline quantity of oxygen-17, thereby establishing the baseline quantity of oxygen-17 based on the quantity of oxygen-17 comprising the external atmosphere of the enclosure.

5. The method of claim 3 further comprising individually evaluating a plurality of objects by:
    collecting the plurality of objects where each object resides within an interior of an individual enclosure and where an individual surrounding atmosphere contacts the each object and resides in the interior of the individual enclosure, where the individual surrounding atmosphere comprises nitrogen-14;
    labeling one of the objects comprising the plurality of objects as a first object;
    evaluating the first object by:
        sampling a first surrounding atmosphere, where the first surrounding atmosphere is the individual surrounding atmosphere contacting the first object, thereby sampling the surrounding atmosphere and thereby collecting the atmospheric sample; and
        performing the analyzing, comparing, and designating steps of claim 1 using the first object as the object, thereby designating the first object as the potentially irradiated object or the non-potentially irradiated object; and selecting a second object comprising the plurality of objects and repeating the sampling a first surrounding atmosphere step and the performing the analyzing, comparing, and designating steps of claim 1 step using the second object as the first object until every object in the plurality of objects has served as the first object, thereby individually evaluating the plurality of objects.

6. The method of claim 3 where analyzing the atmospheric sample with the atmospheric analyzer comprises transferring at least some portion of the atmospheric sample to a mass spectrometer and conducting a mass spectroscopy of the at least some portion of the atmospheric sample using the mass spectrometer.

7. The method of claim 3 where analyzing the atmospheric sample with the atmospheric analyzer comprises transferring at least some portion of the atmospheric sample to a nuclear magnetic resonance spectrometer and conducting a nuclear magnetic resonance spectroscopy of the at least some portion of the atmospheric sample using the nuclear magnetic resonance spectrometer.

8. The method of claim 3 where analyzing the atmospheric sample with the atmospheric analyzer comprises transferring at least some portion of the atmospheric sample to a gas chromatograph and conducting a gas chromatography of the at least some portion of the atmospheric sample using the gas chromatograph.

9. The method of claim 1 further comprising:
communicating the quantity of oxygen-17 in the atmospheric sample from the atmospheric analyzer to a digital processor;
comparing the quantity of oxygen-17 in the atmospheric sample to the baseline quantity of oxygen-17 using the digital processor;
generating an alert signal if the quantity of oxygen-17 in the atmospheric sample is greater than the baseline quantity of oxygen-17 using the digital processor; and
transmitting the alert signal from the digital processor to an alarming device and providing an alarm when the alert signal is received by the alarming device, thereby designating the object as the potentially irradiated object if the quantity of oxygen-17 in the atmospheric sample is greater than or equal to the baseline quantity of oxygen-17.

10. The method of claim 9 where the object and the surrounding atmosphere reside in an interior of an enclosure and where an external atmosphere comprising nitrogen-14 is in contact with an exterior of the enclosure and further comprising:
sampling the external atmosphere thereby generating an external atmospheric sample;
analyzing the external atmospheric sample with the atmospheric analyzer and determining a quantity of oxygen-17 in the external atmospheric sample;
communicating the quantity of oxygen-17 in the external atmospheric sample from the atmospheric analyzer to the digital processor; and
establishing the quantity of oxygen-17 in the external atmospheric sample as the baseline quantity of oxygen-17 using the digital processor.

11. A system for inspecting an object for possible irradiation exposure comprising:
a sampling line withdrawing an atmospheric sample from a surrounding atmosphere contacting an object, where the surrounding atmosphere comprises nitrogen-14;
an atmospheric analyzer configured to receive the atmospheric sample and determine a quantity of oxygen-17 in the atmospheric sample;
a digital processor in data communication with the atmospheric analyzer and the digital processor programmed to perform steps comprising:
receiving the quantity of oxygen-17 in the atmospheric sample from the atmospheric analyzer;
comparing the quantity of oxygen-17 in the atmospheric sample to a baseline quantity of oxygen-17; and
generating an alert signal if the quantity of oxygen-17 in the atmospheric sample is greater than the baseline quantity of oxygen-17; and
an alarming device in data communication with the digital processor and the alarming device configured to receive the alert signal and provide an alarm in response to the alert signal, thereby inspecting the object for possible irradiation exposure.

12. The system of claim 11 further comprising the atmospheric analyzer in fluid communication with the sampling line.

13. The system of claim 11 further comprising:
the sampling line withdrawing the atmospheric sample from an interior of an enclosure;
a second sampling line in fluid communication with an external atmosphere in contact with an exterior of the enclosure;
the atmospheric analyzer configured to receive an external atmospheric sample from the second sampling line and determine a quantity of oxygen-17 in the external atmospheric sample; and
the digital processor further programmed to perform steps comprising:
receiving the quantity of oxygen-17 in the external atmospheric sample from the atmospheric analyzer; and
designating the quantity of oxygen-17 in the external atmospheric sample as the baseline quantity of oxygen-17, thereby receiving the baseline quantity of oxygen-17 from the atmospheric analyzer.

14. The system of claim 13 further comprising the atmospheric analyzer in fluid communication with the second sampling.

15. The system of claim 11 where the atmospheric analyzer comprises at least one of a mass spectrometer, a nuclear magnetic resonance spectrometer, a gas chromatograph, or combinations thereof.

16. A method of inspecting a plurality of objects for possible irradiation exposure comprising:
establishing a baseline quantity of oxygen-17 by:
sampling an external atmosphere, where the external atmosphere comprises nitrogen-14, thereby collecting an external atmospheric sample;
analyzing the external atmospheric sample with an atmospheric analyzer and determining a quantity of oxygen-17 in the atmospheric sample; and
designating the quantity of oxygen-17 in the atmospheric sample as a baseline quantity of oxygen-17, thereby establishing the baseline quantity of oxygen-17;
collecting a plurality of objects where each object resides within an interior of an individual enclosure and where an individual surrounding atmosphere contacts the each object and resides in the interior of the individual enclosure, and where the individual surrounding atmosphere comprises nitrogen-14;

labeling one of the objects as a first object;
evaluating the first object by:
- sampling a first surrounding atmosphere, where the first surrounding atmosphere is the individual surrounding atmosphere contacting the first object, thereby establishing a first atmospheric sample;
- analyzing the first atmospheric sample with the atmospheric analyzer, and determining a quantity of oxygen-17 in the first atmospheric sample;
- comparing the quantity of oxygen-17 in the first atmospheric sample to the baseline quantity of oxygen-17;
- designating, if the quantity of oxygen-17 in the first atmospheric sample is greater than the baseline quantity of oxygen-17, the first object as a potentially irradiated object, or designating, if the quantity of oxygen-17 in the first atmospheric sample is equal to or less than the baseline quantity of oxygen-17, the first object as a non-potentially irradiated object;

selecting a second object comprising the plurality of objects and repeating the sampling step, the analyzing step, the comparing step, and the designating step using the second object as the first object until every object in the plurality of objects has served as the first object, thereby inspecting the plurality of objects for possible irradiation exposure.

17. The method of claim 16 further comprising:
communicating the baseline quantity of oxygen-17 from the atmospheric analyzer to a digital processor;
communicating the quantity of oxygen-17 in the first atmospheric sample from the atmospheric analyzer to the digital processor;
comparing the quantity of oxygen-17 in the first atmospheric sample to the baseline quantity of oxygen-17 using the digital processor;
generating an alert signal if the quantity of oxygen-17 in the first atmospheric sample is greater than the baseline quantity of oxygen-17 using the digital processor; and
transmitting the alert signal from the digital processor to an alarming device and providing an alert on the alarming device when the alert signal is received by the alarming device, thereby designating the first object as the potentially irradiated object if the quantity of oxygen-17 in the first atmospheric sample is greater than or equal to the baseline quantity of oxygen-17.

18. The method of claim 17 where analyzing the first atmospheric sample with the atmospheric analyzer comprises transferring at least some portion of the first atmospheric sample to a mass spectrometer and conducting a mass spectroscopy of the at least some portion of the first atmospheric sample using the mass spectrometer.

19. The method of claim 17 where analyzing the first atmospheric sample with the atmospheric analyzer comprises transferring at least some portion of the first atmospheric sample to a nuclear magnetic resonance spectrometer and conducting a nuclear magnetic resonance spectroscopy of the at least some portion of the first atmospheric sample using the nuclear magnetic resonance spectrometer.

20. The method of claim 17 where analyzing the first atmospheric sample with the atmospheric analyzer comprises transferring at least some portion of the first atmospheric sample to a gas chromatograph and conducting a gas chromatography of the at least some portion of the first atmospheric sample using the gas chromatograph.

* * * * *